US007563616B2

(12) United States Patent
Gillis et al.

(10) Patent No.: US 7,563,616 B2
(45) Date of Patent: Jul. 21, 2009

(54) BACTERIAL LETHALITY TEST INDICATOR AND PROMPT RESPONSE SPECTROSCOPIC ANALYZER

(76) Inventors: John R. Gillis, 2303 Nelson Rd., Bozeman, MT (US) 59715; Kathleen A. Hickey, 311 1/2 N. Grand, Bozeman, MT (US) 59715; Darlene Hartze, 24515 Frontage Rd., Bozeman, MT (US) 59718; Douglas Peterson, 700 Painted Canyon Dr., Bozeman, MT (US) 59718

( * ) Notice: Subject to any disclaimer, the term of this patent is extended or adjusted under 35 U.S.C. 154(b) by 744 days.

(21) Appl. No.: 10/954,478

(22) Filed: Oct. 1, 2004

(65) Prior Publication Data

US 2005/0074833 A1 Apr. 7, 2005

Related U.S. Application Data

(60) Provisional application No. 60/508,087, filed on Oct. 2, 2003.

(51) Int. Cl.
*C12M 1/34* (2006.01)
*C12M 3/00* (2006.01)
*C12M 1/24* (2006.01)
*B01L 3/00* (2006.01)

(52) U.S. Cl. ............... 435/287.4; 435/31; 435/288.1; 435/288.3; 435/299.2; 435/304.1; 435/287.6; 435/288.7; 422/99; 422/102; 422/913

(58) Field of Classification Search ............... 435/287.4, 435/31, 288.1, 288.3, 299.2, 304.1, 287.6, 435/288.7

See application file for complete search history.

(56) References Cited

U.S. PATENT DOCUMENTS

| 3,814,522 | A | * | 6/1974 | Clark et al. | .................. | 356/246 |
| 5,710,041 | A | * | 1/1998 | Moorman et al. | ......... | 435/287.6 |
| 6,063,591 | A | * | 5/2000 | Bolea | .......................... | 435/31 |
| 6,623,955 | B2 | * | 9/2003 | Matner et al. | ............ | 435/287.4 |
| 2002/0115131 | A1 | * | 8/2002 | Witcher et al. | ................. | 435/31 |

* cited by examiner

*Primary Examiner*—William H Beisner
*Assistant Examiner*—Nathan A Bowers (57) ABSTRACT

Multiple-component integral-structure dual-test sterility indicator, method of assembling physical components, selected spores, and chemical constituents in solution, within the indicator and arranged to enable dual-evaluations of bacterial-lethality of a dry-goods load, resulting from exposure to a selected saturated-steam sterilizing cycle. The chemical constituents are formulated to chemically produce reaction-product, which is quantitatively responsive to the combined effect of cycle steam temperature and time of exposure at that temperature, for providing a promptly-available spectroscopic evaluation of bacterial-lethality. Absorption of narrow-band selected visible-light wavelength by reaction-product, if any, of chemical-constituent solution, is used to quantitatively measure that combined-effect exposure. Subsequent to such prompt-response evaluation of bacterial-lethality, a biological evaluation of bacterial-lethality, utilizing the confined contents of the same test indicator, free of risk of ambient contamination of any such contents, by evaluating pH change, if any, due to live spore-growth, or the absence thereof, following a predetermined spore incubation period, utilizing the exposed liquid constituent-solution for such spore-culturing evaluation.

2 Claims, 7 Drawing Sheets

ANALYZER WARMING TO 37°C

FIG. 7B

OPERATOR ENTERS CYCLE PARAMETERS

FIG. 7C

OPERATOR INSERTS UNIT INTO THE SAMPLER CHAMBER

FIG. 7D

ANALYZER BRINGS SAMPLE TO 37°C

FIG. 7E

ANALYZER READS TRANSMITTANCE THROUGH EMPTY CURETTE THEN ACTIVATES UNIT.

FIG. 7F

ANALYZER READS TRANSMITTANCE OF SAMPLE

BACTERIAL LETHALITY TEST INDICATOR AND PROMPT RESPONSE SPECTROSCOPIC ANALYZER

RELATED APPLICATION

This application claims the benefit of U.S. Provisional Patent Application Ser. No. 60/508,087 filed Oct. 2, 2003.

INTRODUCTION

This invention relates to evaluating bacterial-lethality effectiveness of a saturated-steam sterilizing cycle by integrating components of a test-indicator so as to be capable of prompt-response spectroscopic chemometric evaluation of bacterial-lethality, while also being capable of providing for subsequent spore-culturing and biological evaluation of bacterial-lethality; and, more particularly, is concerned with methods and structures which directly correlate those evaluations of bacterial-lethality by carrying out and completing both said evaluations while materials, including liquid-contents and spores remain in a single integral-structure sterility indicator, free of an opportunity for ambient-contamination during such evaluations.

OBJECTS OF THE INVENTION

One object is selecting a formulation for a solution of carbohydrates which reacts chemically responsively to temperature and time at that temperature exposure, during a selected saturated-steam sterilizing cycle, so as to form a reaction-product capable of spectroscopic-quantitative chemometric measurement using visible-light spectra.

A related object is selectively formulating an aqueous solution of organic materials capable of providing a spectroscopic quantitative chemometric evaluation of temperature and time at that temperature, of a selected saturated-steam cycle, which evaluation is available promptly upon cool-down following exposure to a selected saturated-steam sterilizing cycle.

A further related object is providing a multiple-component integral test-indicator which is capable of providing a prompt-response spectroscopic evaluation of bacterial-lethality and, additionally, capable of biological-evaluation of bacterial-lethality for validating the spectroscopic evaluation of bacterial-lethality.

Another object is providing a method of assembly of an integral-structure for positioning mechanical components with selected physical characteristics, chemically-responsive constituents, and bacterial-spores in a single sterility indicator so as to enable correlating spectroscopic chemometric and biological bacterial-lethality evaluations of a selected saturated-steam sterilizing cycle, while such components, spores, and constituents remain in the single sterility indicator for those dual evaluations of bacterial-lethality.

An attendant object is to provide methods and equipment enabling short-interval turn-around times while facilitating accurately carrying out spectroscopic-chemometric evaluations of multiple exposed test indicators.

An additional object is to provide manually-operable structure, for fracturing a sealed glass ampoule within an integral-structure test indicator for releasing liquid-contents after carrying-out a selected saturated-steam cycle, for initiating spectroscopic chemometric quantitative analyses of temperature and time at that temperature exposure for prompt-response evaluation of bacterial-lethality; and, for subsequently correlating biological-evaluation of bacterial-lethality due to exposure to the selected saturated-steam sterilizing cycle.

Other objects and contributions will be described in relation to embodiments of the invention shown in the accompanying drawings.

BRIEF DESCRIPTION OF THE DRAWINGS

FIG. 5A' is a side-elevation view of the entrance-opening at the open-end of FIG. 5A, prior to initiating use for spectroscopic-chemometric measurements and subsequent biological-evaluation of the invention;

FIG. 5A" is a side-elevation view of the FIG. 5A entrance-opening entrance-opening, as opened to enable receiving a test indicator of the invention, for initiating planned spectroscopic measurements of bacterial-lethality;

DETAILED DESCRIPTION

Prior existing "tell-tale" type of test devices for thermal sterilizing cycles indicate when a preselected temperature has been reached in a sterilizer chamber. Those test devices have been used for thermal sterilizing cycles since early in the first half of the twentieth century; and, rely on a material which melts, or otherwise changes physically upon reaching a designated temperature; when such a test material reached a certain temperature, the change in appearance would be readily apparent later to a thermal-sterilizer operator.

Saturated-steam cycles utilize moist-heat at a selected temperature for facilitating spore-lethality. However, spore lethality when utilizing a saturated-steam sterilizing cycle is dependent on attaining the selected cycle temperature, and on maintaining that temperature for time requirements; which are established by standards approved by the American Association of Medical Instrumentation (AAMI) for a selected-temperature cycle. For example, when an elevated saturated-steam temperature of 250° F. (121° C.) is selected, the time at that temperature for that selected cycle is twelve to fifteen minutes.

That temperature must be maintained with exposure of the sterilizer load, for prescribed time-interval, in order to assure "killing" of the most difficult-to-kill bacterial spores to be encountered in a dry-goods sterilizer load. Such a dry-goods load could include, after removal of common types of soil of surgical instruments, surgical garments, clothe, and the like, used in hospitals or other health-providing institutions. Other types of dry-goods loads could include pharmaceutical items or equipment, as commercially distributed after carrying out a selected saturated-steam sterilizing cycle during industrial sterilization.

The dependent temperature and time at that temperature relationship, and the requirements for saturated-steam sterilizing-cycles have been analyzed for developing concepts for improved testing methods, associated test structures, testing apparatus, and systems for coordinating testing and correlating results. In particular systems combining means for biological-validation of an earlier determined temperature, and time at that temperature, effect of a selected saturated-steam sterilizing cycle; and, for accurately determining, by spectroscopic quantitative chemometric measurements, the bacterial-lethality as obtained, promptly after exposure to a selected saturated-steam cycle.

Bacterial-lethality involves "destruction" of spores; that is: not only "killing" of spores but, also, rendering spores incapable of reproducing. Biological testing for bacterial-lethality of a saturated-steam cycle had been maintained as a requirement for health-care providing institutions by the Federal Food and Drug Administration (FDA). Biological-testing of bacterial-lethality has previously required substantial specific handling; in particular, subsequent to exposure in preparing for and maintaining spore-culturing conditions for exposed spores during culturing periods extending from two to about seven days.

Previous practice had required that bacterial spores be embedded in conveniently-sized cut-out paper; each such paper was then sealed in a glassine envelope; and, multiple sealed envelopes were distributed within a sterilizer load, prior to start of a cycle. Then, following exposure and culturing for two to seven days, biological-evaluation of spore lethality took place; that has remained a requirement for hospitals, and other health-service institutions, before permitting goods from a sterilizer-load to be returned, for normal usage, after completion of a saturated-steam sterilizing cycle.

Those procedures involve rigid and demanding control steps for each of the following: (i) preparation of the spore-bearing paper, and of each glassine envelope used for biological-testing, (ii) special storage handling of those glassine packets, (iii) sterile handling of those packets in preparation for placement in and after a sterilizing cycle, and, (iv) special handling steps and procedures to avoid any ambient contamination in preparing for and in the culturing of the spores of those packets, after sterilizer-cycle exposure. Such extended time-consuming procedures and demanding handling requirements continue to be maintained for biological-testing of the effectiveness of a saturated-steam sterilizing cycle for above-named goods used in hospitals, and like health-care institutions.

Present concepts diminish the opportunity, and potential sources, for unintentional ambient-contamination, while providing for a biological evaluation of bacterial-lethality. Structural and assembly concepts for the test indicator of the invention provide for and carry-out control-procedures during assembly of the multiple components of the dual-test indicator which scientifically eliminate the above-described sequentially-repeated sterile handling steps procedures, subsequent to exposure. Resulting in facilitating and implementing the accuracy of biological-evaluations bacterial-lethality; and, supplement the functions of a single test indicator, by providing dual-evaluations of bacterial-lethality in accordance with the invention.

A possible contribution of an accurate prompt-response evaluation of bacterial-lethality, can be a forewarning that difficult, or questionable, sterilizing conditions existed at a particular location in a sterilizer chamber; or, a forewarning that an institute's standard cycle could use some modification. The spectroscopic evaluation of a cycle's temperature and the time at that temperature are available, following completing a selected saturated-steam sterilizing cycle, upon cool-down sufficient to permit load handling. A controlled-temperature has been found to be important in order to obtain a prompt and accurate spectroscopic-chemometric-evaluation of bacterial-lethality. That evaluation can be carried-out prior to initiating any of the time-consuming spore-nurturing procedures and, thus, provides an early notice of possible difficulties or desired results which are to be verified by a biological-evaluation.

An aqueous-solution of carbohydrates has been devised, and selectively-formulated, for use both in said prompt-response spectroscopic-evaluation of bacterial-lethality and in the later biological-evaluation of bacterial-lethality. The selectively formulated solution contributes the ability to carry-out both such evaluations while components, spores, and constituents remain in a single integral-structure dual-test indicator protected against ambient-contamination.

Assembly concepts involve placement of said multiple components, spores, and materials in an integral-structure; with provisions made for later timely controlled-release of the selectively-formulated aqueous solution of chemical constituents, after cycle exposure. In the procedures taught herein, sealing of that chemically-formulated solution, releasing for spectroscopic-evaluation, and, for later spore-cultured biological-evaluation of bacterial-lethality are physically-correlated by use of the same liquid-contents as sealed within the integral-structure of the test indicator. Both a prompt spectroscopic-bacterial-lethality evaluation and a subsequent biological-evaluation of bacterial-lethality are carried out while contents are protected within a single sterility indicator structure; relying on assembly concepts of said single structure functioning so as to correlate both those evaluations. Present assembly concepts also contribute a relationship, during exposure to the sterilizing cycle, in which the enclosed spores and the specially-formulated solution are not in contact with each other during exposure experienced in carrying-out the selected saturated-steam sterilizing cycle.

Carbohydrate constituents are specially-formulated to be responsive to saturated-steam cycle temperature exposure and to the selected time at that temperature, as experienced where the test indicator is located within a sterilizer load during the cycle. Those constituents are formulated to provide a reaction-product for accurately measuring bacterial-lethality, of selected enclosed spores, by utilizing spectroscopic-chemometric quantitative measurement of that reaction-product, if any; such that the solution provides for a prompt-response evaluation of bacterial-lethality of a designated number of selected spores within the indicator; and, those spores are selected to be those most resistant to lethality. Also, both the solution, as formulated, and the solution containing reaction-product, if any after partial or complete intended exposure during the cycle, are both capable of spectroscopic evaluation; and, also, capable of nurturing live spores, if any, for biological-evaluation of bacterial-lethality. The selected spores and the solution, as formulated or the reaction-product solution, remain protected within the same test-indicator structured for both such evaluations of bacterial-lethality.

By providing for both the chemical solution as formulated, and for the solution with reaction-product, if any, after exposure to the saturated-steam cycle, to be capable of culturing spore growth implements directly correlating the spectroscopic evaluation of bacterial-lethality and the subsequent biological-evaluation of bacterial lethality for validating the spectroscopic evaluation. That is, spectroscopic measurement of bacterial-lethality is carried-out promptly after exposure to the selected-temperature and time at that temperature, as experienced where the dual-test indicator is located in the sterilizing chamber; and, provides early forewarning of any discrepancy, or a validation of both the chemometric evaluation of spore lethality by the biological-evaluation of bacterial-lethality; and both are carried-out and completed, while components, spores, and constituents are protected within the same test indicator; thus, both directly correlating evaluations free of risk of ambient contamination.

FIGS. 1 and 2 are disassembled views for describing the multiple components, their configurations, types of materials used in fabricating those components, liquid-media constituents, and assembly of the multiple-components into an integral-structure dual-test sterility indicator of the invention; the assembled view of those components and constituents is shown in FIG. 3. Throughout the detailed description of the accompanying drawings, like reference numbers are used in referring to like portions of the test-indicator, spectroscopic-analyzing equipment, and mechanical structures used in carrying-out the dual bacterial-lethality evaluations of the invention.

In the pre-assembly view of FIG. 1, one-piece cup-shaped polymeric-material closure cap 14 includes a sidewall interior with circumferential profiling rings. Those decreased-diameter profiling rings 15, 16 are located about midway of the interior side wall height of closure cap 14; and, in combination with cup-shaped filter 17 enable desired protection, for the integral-structure components and contents, at the closure-cap longitudinal end of unitary elongated generally-tubular container 18 for carrying out the invention.

Cup-shaped filter 17, is fitted within closure cap 14 so as to establish contact between the cup-shaped filter 17 end-wall and the interior surface of the closed end wall of closure cap 14; providing covering for the apertures defined in the closure cap end wall. That positioning and relationship can be better visualized from the assembled view of FIG. 3. The material for, and the cross-section thickness of, filter 17 are selected so as to provide a tortuous-path cross-sectional thickness, to prevent entry into or exit from, both spores and liquids through the limited number of apertures distributed in the end-wall of polymeric cap 14.

Access of saturated-steam into the elongated unitary container 18 is provided through the apertures defined in the otherwise solid end-wall surface of closure cap 14; and, also egress of air is provided by said apertures. The limited number of apertures are distributed, as shown in the top-plan view of cap 14 of FIG. 2, to facilitate said saturated-steam access into, and gas egress from, elongated longitudinally-oriented passageways which are defined within unitary container 18, and later described in more detail. Interfitting filter 17, precludes access, or egress, of spores, liquid, combinations thereof; thus providing desired protective closure for the assembled multiple-component dual-test integral-structure 19, shown in FIG. 3, while providing for the desired action of saturated steam within unitary container 18, as discussed below.

An elongated unitary thin-glass sealed ampoule 20, as best seen in FIG. 1, includes the above-described specifically-formulated aqueous solution 21 of organic-chemical-constituents; and, includes an organic pH indicator, the function of which is later described in more detail. Ampoule 20 is supported longitudinally within the elongated generally-tubular-configuration portion of one-piece container 18. The interior of container 18 is generally-tubular throughout its main-body extending longitudinally from closure cap 14, to a location for a unitary rectangular cubic-shape, at unitary closed longitudinal end of container 18. Protrusions on that interior surface configuration of the largely tubular portion, help to provide an upright position for elongated sealed-glass ampoule 20. Structural-assembly concepts of container 18 of indicator 19 are to predispose components so as to control the actual movement of saturated-steam within elongated container 18, in contact with ampoule 20; and, for later providing for release of ampoule liquid-contents so as to facilitate reliable, separately-conducted, and directly correlated, dual-evaluations of spore lethality. For that objective, the spores are separately positioned from the sealed liquid-contents of ampoule 20, during cycle exposure, and prior to the prompt-response spectroscopic evaluation of bacterial-lethality.

Polymeric material for elongated unitary container 18 is selected to meet strict transmittance requirements; that is, to be “distortion-free” in transmitting visible light within a designated narrow-beam wavelength 405 nm, 420 nm, and 430 nm. The polymer for container 18 must also be capable of withstanding sterilization temperatures and air-evacuation conditions of a selected saturated-steam sterilizing cycle; while continuing to provide for desired predisposition of components, impact-resistance, mechanical strength, and sufficient flexibility for carrying out post-exposure steps of the invention.

Figure 1:
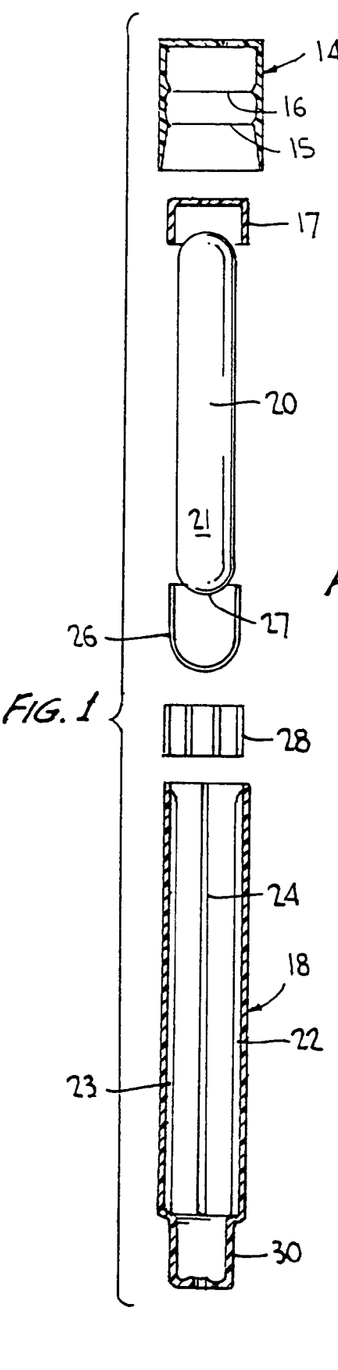
FIG. 1 is a pre-assembly vertically-oriented cross-sectional view of an integral structure multiple-component of a test-indicator of the invention, for describing those components and other materials used for dual-evaluations of sterilizing effectiveness, upon completion of a saturated-steam sterilizing cycle.

During molding of a specified polymeric material for unitary container 18 internally-located longitudinally-elongated protrusions, which are bead-like in cross-sectional configuration, are positioned along an extended-length of the interior generally-tubular configuration portion of elongated-container 18. Radially-inwardly-protruding longitudinally-extending internal ribs 22, 23, and 24 are shown in FIG. 1; and, are shown in cross-section as 22, 23, 24, and 25 in FIG. 2. Those protrusions contribute multiple desired side wall capabilities by, for example: (i) adding to side wall thickness at selective locations; (ii) providing longitudinal support for, and contact with, elongated ampoule 20 which is longitudinally-oriented as shown; and, (iii) providing columnar-space between intermediate ribs 22 through 25 and the outer peripheral of ampoule 20, along the interior of the elongated tubular portion of container 18. That columnar-space enables active lengthwise movement of saturated-steam, which is moving in heat-exchange contact with the exterior surface of ampoule 20 containing liquid-media 21; and, also, provide for lengthwise movement of air, being replaced by saturated-steam during a sterilizing cycle, for egress through apertures as distributed in the end-wall of closure cap 14.

Retainer-sieve 26 presents a U-shape, as seen in the cross-sectional of view FIG. 1. Elongated retainer legs are positioned to extend along and adhere to external side wall portions of elongated ampoule 20. Also, those elongated legs support a centrally-located covering portion for the U-shaped end of retainer-sieve 26; that portion covers the contiguous compound-curvature closed end 27 of ampoule 20; that disposition is better seen in the assembled view of FIG. 3. Retainer-sieve 26 presents a porous polymeric mesh for covering the compound-curvature end 27 of ampoule 20; that polymeric mesh material is selected to be capable of withstanding sterilization temperatures and to be non-reactive chemically with any constituents of the closure-capped unitary container 18. The centrally-located porous mesh portion covering end 27, acts as a screen allowing passage of fluids (liquids or gases), while retaining large-area glass solids; that is, other than powdered or pulverulent portions of compound-curvature 27 when end 27 is fractured, as later described, for release of the liquid-contents of ampoule 20.

An elongated semi-rigid substrate 28 (FIGS. 1, 2) presents an extended-surface-area which is ladened with numerous specified bacterial spores. That substrate material is specifically selected to be non-reactive chemically with contents of unitary container 18. Substrate 28 is also selected to be sufficiently rigid to enable an end-on orientation providing for longitudinal-passage of, and contact with, saturated-steam moving within elongated container 18; and, also providing for passage of later-released liquid-contents of ampoule 20. An example of the desired orientation of spore-ladened substrate 28 is the serpentine configuration; labeled 29 as seen in the "end-on" plan view of FIG. 2. Spore-ladened substrate 28 as end-on oriented in configuration 29, is selected to extend across the horizontal cross-sectional area of the elongated tubular portion of container 18 for supporting ampoule 20. Substrate 28 is located and supported, as best seen in FIG. 3, contiguous to entrance into such unitary end for container 18; providing a rectilinear-configuration cubic-shaped chamber 30 which presents a smaller cross-sectional area, for support of substrate 28, than the generally-tubular portion of unitary container 18.

Four rectilinear side walls and a rectilinear end wall, each preferably of uniform square dimension, define the unitary cubic-shaped closed-end chamber 30 of unitary container 18. The dimensions and configuration selected for chamber 30 establish a diagonal dimension 31 (FIG. 2) which is equal to the internal-diameter dimension of the generally-tubular side wall portion of container 18; which helps to provide for free-movement of later-released contents of ampoule 20 for occupying chamber 30.

Figures 2, 3:
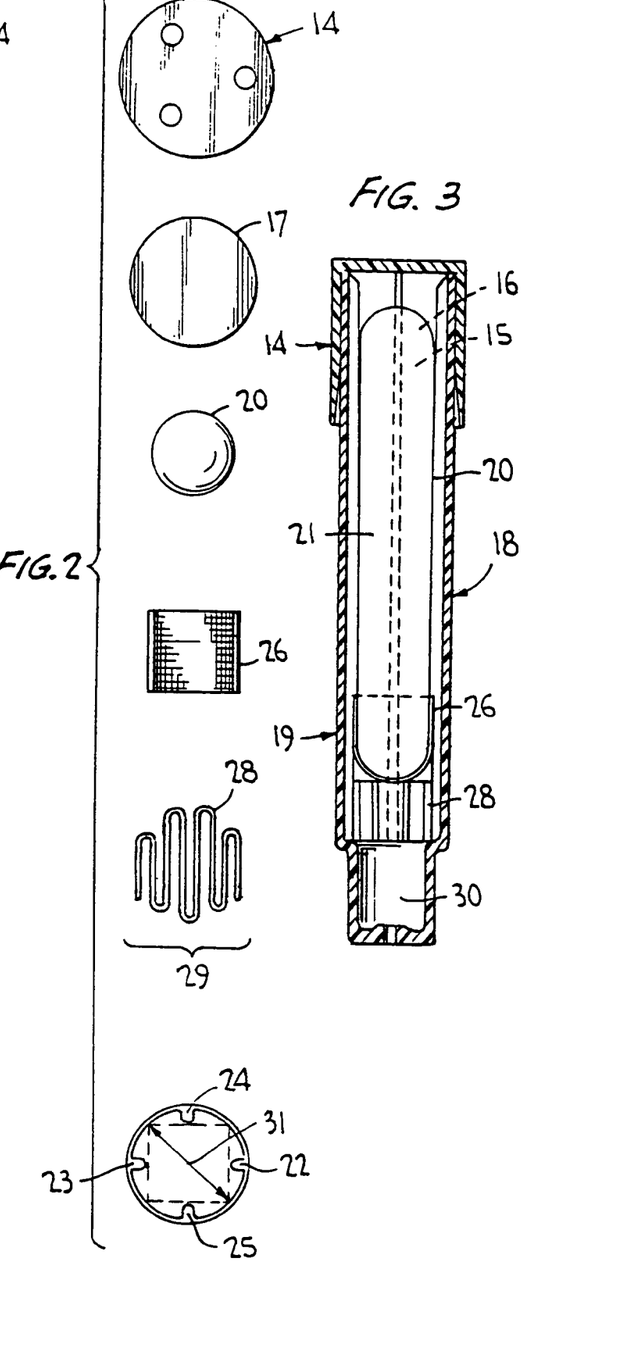
FIG. 2 presents horizontally-oriented top and bottom views of longitudinal ends of selected components, and a traverse cross-sectional view of intermediate components, of the bacterial-lethality test-indicator of FIG. 1, for describing an inter-related positioning orientation of components and materials in accordance with the invention.
FIG. 3 is a vertically-oriented view of the combined multiple-component integral-structure bacterial-lethality test-indicator of FIGS. 1 and 2, shown partially in cross-section, as assembled in accordance with the invention.

Referring to FIG. 3, spore-ladened substrate 28 is positioned across the entrance from the generally-tubular portion of container 18 into the smaller-cross sectional area of cubic-shaped chamber 30. A selected configuration, such as shown at 29 in FIG. 2, enables substrate 28 to straddle, and be supported, contiguous to that entrance into the smaller-cross-section cubic-shaped chamber 30. That positioning provides access to test-chamber 30 for participating in a later-described evaluations of bacterial-lethality sterilizing effectiveness.

Liquid-media 21 is formulated to enable participation in dual-evaluations of spore-lethality. After a selected saturated-steam cycle, glass ampoule 20 is fractured, at compound-curvature end 27, releasing liquid-contents of ampoule 20 within the tubular portion of container 18. Those liquid contents, which are released after exposure experienced during the cycle, occupy test-chamber 30 and cover spore-ladened substrate 28, located as shown in FIG. 3.

Organic chemical constituents of liquid-media 21 are selectively-formulated to provide for spectroscopic measurements of bacterial-lethality; and, also such that the chemical-reaction-product of those constituents, after exposure to an intended saturated-steam sterilizing cycle will also support culturing of live spores (if any). Production of that reaction-product is quantitatively responsive to the cycle temperature, and time at that temperature, experienced by ampoule 20 as assembled in test-indicator 19 (FIG. 3), where the test-indicator is located in a sterilizer load; and, that reaction product is responsive quantitatively to spectroscopic chemometric measurement by utilizing a selected dominant wavelength of visible-light, as set forth above, in a process later described in more detail.

The organic chemical constituents of liquid-media 21 are preferably selected: (i) to be soluble in an aqueous solution, (ii) to chemically respond, without a catalyst, in a manner cumulatively dependent on both temperature and time-at-that-temperature, (iii), responsive to exposure to a saturated-steam sterilizing cycle; and, further (iv) such liquid contents with reaction-product are capable of promoting live spore growth. Such constituents are selected and held in a manner so as to correlate dual bacterial-lethality evaluations resulting from the above-described active-steam exposure, experienced during a selected saturated-steam cycle. Thus, the aqueous solution of organic constituents, as formulated, and the liquid-content reaction product, if any, solution of such an exposure are capable of both spectroscopic evaluation and biological-evaluation of the temperature and time at that temperature, response to the exposure as experienced during a selected saturated-steam sterilizing cycle; and, both the selected formulation and the reaction-product, if any, liquid contents of ampoule 20 enable dual evaluations of bacterial-lethality.

Unitary container 18 of assembled multiple-component test-indicator 19 remains as closed by cap 14. After post-exposure, release of liquid-contents, by fracturing the compound-curvature end 27 of ampoule 20, as later described; in preparation for both such spectroscopic evaluation and biological evaluations of bacterial-lethality. The earlier spectroscopic-evaluation of spore lethality is directly correlated with the later biological-evaluation of spore lethality which relies on culturing live spores, if any. It is significant that multiple-component test-indicator structure 19 as assembled, utilizes unitary container 18 to expose spores in the same manner as spores, in a sterilizer load, are exposed; that is, free of contact with a nurturing solution for cultivating the spores.

*Geo bacillus stearothermophilus* spores, selected as the most resistant organisms known for testing bacterial-lethality, are used in the assembled test-indicator structure 19 (FIG. 3). Selecting such spore-resistance to destruction contributes to the sterilizing efficiency of a saturated-steam cycle, and its evaluation; that is, spores of lower resistance are also destroyed. Saturated steam, preferably, at a temperature selected from the group consisting of at 270° F. and 250° F. for desired moist-heat sterilization. The combinations of temperatures and exposure times for effective saturated-steam sterilizing cycles are later tabulated and discussed. Less resistant spores, such as, *Bacillus subtites var globiegii*, if present, will be "killed" at differing temperature and time at temperature levels than those specified for destruction of the *Geo bacillus stearothermophilus* spores. Also, 100,000 of the latter spores are utilized in a test indicator, to meet standards established by the International Standards Organization (ISO); and, accepted by the American Association of Medical Instrumentation (AAMI) and assigned an AAMI number; which also provides for selected temperature and time at that temperature; which are utilized for spectroscopically determined bacterial-lethality and the biological evaluations of the invention; such that those standards can be used to upgrade standards or systems currently being used at an institution.

The above described cubic-shaped chamber 30 becomes, after release of exposed liquid-contents of ampoule 20, the spectroscopic test-chamber at the unitary closed end of container 18. The dimensional relationships provided within container 18 substantially eliminate any liquid surface tension difficulties by enabling those liquid-contents, as released from ampoule 20, to move readily through the spacing, between the vertically-oriented passageways, of a selected end-on configuration 29 (FIG. 2) for spore-ladened substrate 28, into cubic-shaped test-chamber 30. The spores on substrate 28 are exposed to moist-heat during the selected cycle, as the active saturated-steam moves into and through those passageways provided by configuration 29. And, those exposed spores are later in contact with liquid-contents, as released from ampoule 20, after fracturing the contiguous compound-curved closed end 27 of such ampoule.

Unitary container 18 holds ampoule 20 containing exposed liquid-contents, the spores on substrate 28 are also held within unitary container 18; and, both are raised to a temperature as established, and as held, at a selected location for a test-indicator 19 within the saturated-steam sterilizer load. Air is removed, at least in part, from the sterilizing chamber and from the goods to be sterilized, by the action of evacuating air from the sterilizing chamber. That air removal is also facilitated by the introduction of saturated steam into an upper part of the sterilizing chamber. In an assembled test indicator as shown in FIG. 3, air is removed from unitary container 18 in the same manner by such air evacuation; and, is facilitated by the introduction of saturated steam; the moist heat of which facilitates destruction of the spores on substrate 28. With proper operation of a sterilizer, the selected saturated steam temperature is established by the indication of air removal; and, the selected steam temperature is maintained, after removal of the air during the remaining time of a properly executed cycle in accordance with presently established standards. That is, the time at temperature dependent portion of a selected cycle is carried-out subsequent to the air evacuation, and its replacement by the saturated steam, at the selected temperature for the cycle. Test indicators of the invention are placed at locations, within a sterilizer chamber, where those evacuation objectives are most difficult to establish in a timely manner for carrying out the requirements for assuring efficient and effective bacterial-lethality.

Referring to spectroscopic-analyzing equipment, as schematically-presented in FIG. 4, which is utilized for chemometric quantitative-measurement of the chemical-reaction-product, or the absence thereof, or degree thereof, as experienced by the multiple-component structure 19 at the selected sterilizer-chamber location. A "prompt-response" evaluation of bacterial-lethality is obtained by a spectroscopic quantitative chemometric measurement of the reaction-product glucosamine, if any, the production of which is linearly-responsive to the temperature and time-at-that-temperature experience at the indicator location; and, in the same way as spores of a dry-load experience at that location. That is, such spores are responsive to the temperature and time at that temperature experienced at that location for bacterial-lethality purposes, during a saturated-steam sterilizing cycle. Such temperature and time at temperature requirements of a saturated-steam cycle for meeting bacterial-lethality requirements are, pre-determined and standardized, for the number of designated difficult-to-destroy spores; referred to where, selected for the spore-ladened substrate 28.

Spectroscopic quantitative chemometric analysis is carried-out utilizing visible light spectra, preferably carried-out with a dominant wavelength selected from the group consisting of 405 nm, of 420 nm, and 430 nm. Absorption of the selected wavelength, by the reaction product, if any, is measured at the selected visible-light wavelength. Carbohydrates as formulated include glucose and a relatively high concentration of soytone, provide amino acids reacting with glucose to produce glucosamine; which is formed responsive to the temperature and time at that temperature. Other constituents are also included to bathe nurturing spore growth; glucosamine is produced in response to the exposure to a selected saturated-steam cycle; both with and without reaction produce the liquid-contents of ampoule 20, after exposure, are capable of supporting growth of live spores, if any.

Further, an organic pH indicator Bromcresol Purple is included in the formulated aqueous solution of organic materials sealed in ampoule 20. Bromcresol Purple is for biological-testing of spore growth; (i) it does not diminish the ability of released contents of ampoule 20 to provide prompt-response spectroscopic-chemometric measurement of bacterial-lethality, and (ii) does not diminish the capability of that solution to culture live spore growth for biological-evaluation of spore lethality, regardless of the exposure experienced by the solution of sealed ampoule 20 as held within container 18.

Bromcresol Purple pH indicator is responsible for presence or the absence of a color change to yellow, during culturing of the exposed spores (38) by the liquid-contents released from ampoule. That biological-evaluation of bacterial-lethality validates an earlier spectroscopic evaluation. Utilizing Bromcresol Purple pH indicator detects spore growth resulting from nourishment of live bacteria, if any; due to the change in pH resulting from spore growth; and, the accompanying change of color, if live spores are present, is available directly by ordinary visual observation. That is, saturated-steam exposure if selected and executed in accordance with present standards destroys the 100,000 spores on substrate 28, making it impossible to nurture spore growth. If otherwise, the solution changes color to yellow because of a change in pH, responsive to spore growth during nurturing of any live spores, by the released liquid-contents of ampoule 20; which invalidates the cycle executed.

A direct correlation of spectroscopic-quantitative-chemometric evaluation of liquid-contents, as released from ampoule 20 and, the biological-evaluation by subsequent provision of spore nurturing conditions, are both provided utilizing enclosed contents of the same dual-test indicator of the invention; where that indicator is located in a load. That direct correlation based on contents enclosed within a single unitary container 18, qualifies designation of the assembled indicator 19 of FIG. 3 as a "biological" test-indicator.

Figure 4:
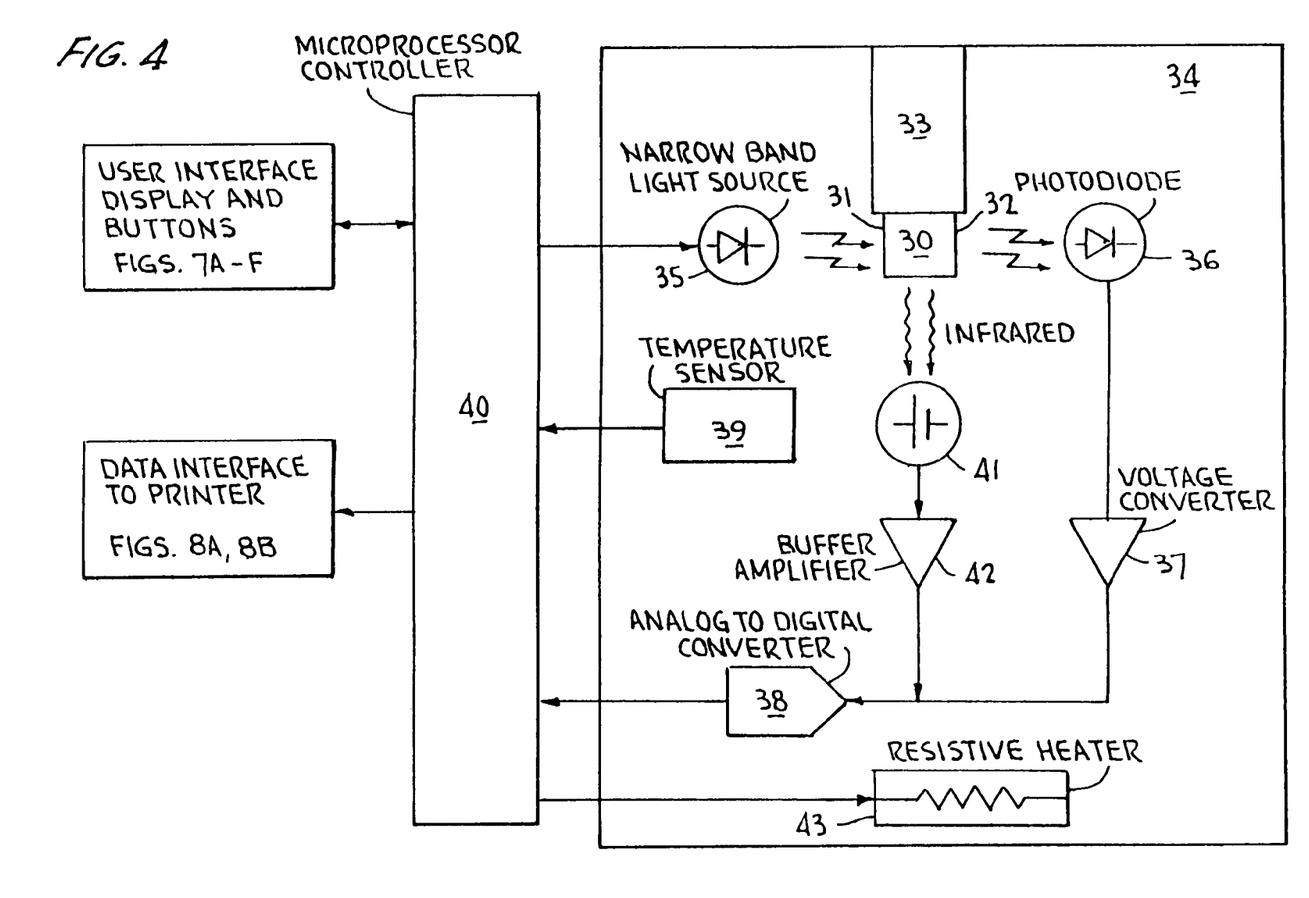
FIG. 4 is a schematic general arrangement view for describing selected optical and inter-related operational equipment for controlling and facilitating recording and output of data, during spectroscopic evaluations of bacterial-lethality of a saturated-steam sterilizing cycle in accordance with the invention.

FIG. 4 schematically depicts optical, electrical, temperature-control, and operational equipment, utilizing a microprocessor control, for spectroscopic quantitative-chemometric measurement(s) utilizing container 18. Provisions are made for measurements at a controlled uniform temperature for each such indicator used in a cycle. That control of temperature facilitates accuracy and consistency of spectroscopic measurements evaluating spore-lethality. In particular, the multiple-components and contents are held within a conforming-configuration of the generally-tubular exterior wall container 18. The parallel opposed planar side-walls 31, 32 of cubic test-chamber 30, as shown in FIG. 4, avoid distortion of solely a dominant visible-light wavelength as selected, and contribute to accurate spectroscopic measurements of absorption of such visible light by liquid-contents which occupy cubic-test chamber 30 upon release from ampoule 20.

Subsequent to completion of an intended saturated-steam cycle, the sterilizer load is cooled down to a temperature which is approximately that selected for consistent spectroscopic chemometric measurement purposes. An exposed test-indicator is held at approximately one hundred degrees Fahrenheit, within a conforming-configuration chamber 33 of controlled-temperature metal block 34 for prompt-response spectroscopic analysis of bacterial-lethality. Provisions are made for short-interval turn-around times for multiple test indicators. Spectroscopic measurements are carried out at a temperature of thirty-seven degrees Centigrade, plus or minus one degree Centigrade. A test indicator is inserted into chamber 33 such that the cubic-shaped test-chamber 30 extends from the otherwise conforming-configuration of chamber 33. Spectroscopic-chemometric quantitative measurements are carried out using a selected narrow-width band of visible light; of a dominant wavelength selected from the group consisting of 405 nm, 420 nm, or 430 nm.

In FIG. 4, LED light source 35 projects a selected narrow-band wavelength visible-light through planar side walls 31, 32, of chamber 30, before any release, as later described, of liquid-contents from ampoule 20. Photodiode 36 quantitatively measures visible light passage through cubic panels 31, 32; which is directed to voltage converter 37, for analog to digital conversion. However, before any reference-reading or any spectroscopic measurements, the coincidence between the temperature of the indicator and block 35 continues to be verified. Temperature sensor 39 verifies the temperature of block 34, which is directed to and processed by microprocessor 40 for the functions designated in FIGS. 7A-F and FIGS. 8A-B, as later described. Thermopile 41 is used for determining any differences between the desired 37° Centigrade ±1° Centigrade temperature for test-chamber 30 and that of block 34. Any temperature difference determined by thermopile 41 is directed through buffer amplifier 42 for, for direction to microprocessor 40, which controls block heater 43.

After determination of the reference-reading, the test indicator 19 is removed from chamber 34, for release of the liquid-contents of ampoule 20 by use of a manually-operated fracturing structure of the invention, as described below in relation to FIGS. 5A, 5A', 5A", 5B, and 5C. That structure fractures the compound-curvature end 27 (FIG. 1) of ampoule 20, which is supported by configuration 29 spore-ladened substrate 28 (FIG. 2); for releasing liquid-contents of ampoule 20 to occupy test-chamber 30, as well as covering spore-ladened substrate 28. Providing a manually-operated fracturing structure simplifies and improves the procedure for fracturing sealed ampoule 20 specifically at compound-curvature distal end 27, so as to utilize sieve means 26, as previously described, to prevent any large pieces of fractured glass which might distort spectroscopic chemometric measurements from entering cubic-shaped test-chamber 30.

Manually-operable structure 50 (FIG. 5A) for fracturing glass ampoule 20 is preferably fabricated as a unitary structure from a high-strength polymeric material. Structure 50 presents two elongated substantially-rigid arms 51, 52 extending the full longitudinal length of such arms which are structured at their closed end. By utilizing a selected high-strength polymeric material, arms 51, 52 can be joined by a unitary closed-end joinder 53 providing a hinge-like action for opening and closing movement at the remaining longitudinally-opposite entrance opening end of elongated arms 51, 52; and, also provides for the entrance-opening movement of arms 51, 52 is at least partially-constrained by closed-end joinder 53; however, such open-end movement is specifically limited by interlocking legs 54, 55; as seen in FIGS. 5A, 5B and 5C. Interlocking leg 54 extends from elongated arm 52; and, interlocking leg 55 extends transversely of the elongated opening from arm 51; they function cooperatively, to limit the entrance-opening, from a location adjacent to fixed platform 56. Interlocking legs 54 and 55 extend across a major portion of the transverse internal cross-section, between the elongated arms, at that location; each includes a co-acting interconnecting edge which limits the maximum entrance-opening into the hand-operable structure 50.

Figure 5A:
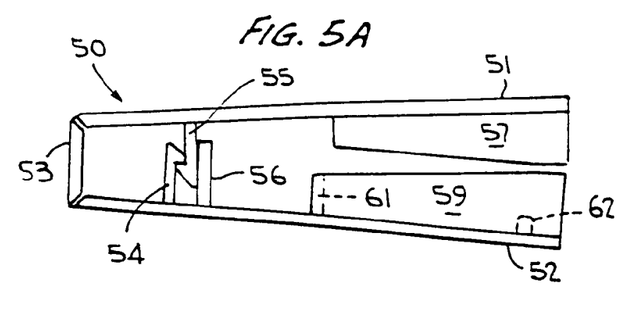
FIG. 5(A) is a schematic side-elevational view of an elongated manually-operable structure of the invention for describing components and their functions in fracturing a unitary glass ampoule in order to release liquid-contents, which had been sealed within an exposed test-indicator, for initiating evaluations of bacterial-lethality in accordance with the invention.
Figure 5B:
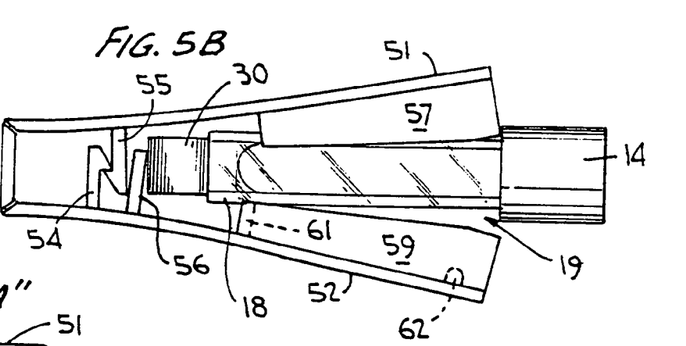
FIG. 5B is a side view of the structure of FIG. 5A and further including a dual-test indicator of the invention for describing location as inserted within the manually-operable structure of FIG. 5A, in preparation for carrying-out a planned release of glass-ampoule contents of the invention.
Figure 5C:
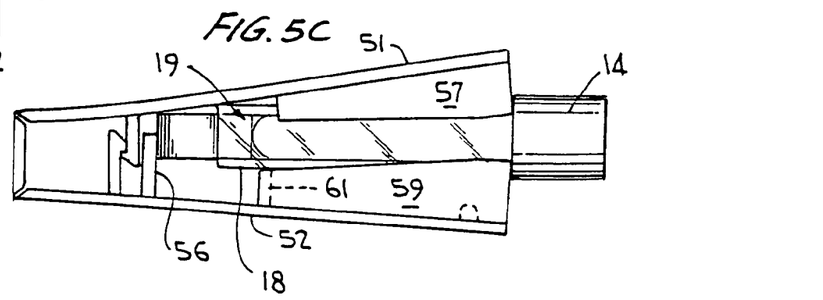
FIG. 5C is a side view of the manually-operated structure of FIG. 5A, including the inserted elongated test-indicator of FIG. 5B, for describing fracturing a compound-curvature end of a sealed glass ampoule, as positioned within the test indicator at a preselected location, for release of ampoule contents in accordance with the invention.

The entrance-opening elevational view of FIG. 5A' is longitudinally-opposite to closed-end joinder 53, and shows an entrance opening leading into the interior of hand-operable structure 50, extending longitudinally between elongated arms 51, 52, as seen in FIG. 5A. FIG. 5A' shows that entrance opening as normally presented, when said structure 50 is in a "stand-by" condition prior to usage. That entrance is partially defined by end-opening portions of elongated arms 51, 52; and, each arm also presents a pair of inter-fitting elongated side walls, respectively 57, 58 on arm 51 and 59, 60 on arm 52; as seen in the side elevation view of FIG. 5A', and, also, in FIG. 5A". The longitudinally-elongated configuration for such side walls can be seen, and best determined, from the side elevational of 57, 59 in FIGS. 5A, 5B and 5C. Side walls 57, 58 on arm 51, inter-fit within arms 59, 60 of arm 52, as best observed in FIG. 5A'. That transverse spacing between those side walls provides for orienting and confining a previously-described elongated unitary container 18, as inserted longitudinally within the entrance-opening; as seen in the elevational view of FIG. 5B.

In FIG. 5B, the test-chamber 30 of elongated unitary container 18, of an assembled dual-test indicator 19 is inserted longitudinally through the entrance opening between side-bars 57, 58 and 59, 60; as seen in the exposed open-end view of FIG. 5A". An inserted indicator extends to where the distal-end of cubic-shaped test-chamber 30 contacts platform 56; at such location, the large-diameter closure cap 14 remains longitudinally exterior to the entrance-opening. Unitary container 18 of test indicator 19, as positioned by platform 56 in FIG. 5B, is in the correct location for fracturing the compound-curvature end 27, as best seen in FIGS. 1 and 3 of ampoule 20.

The held-open entrance-end of structure 50, as seen in FIG. 5A" prior to insertion of a test-indicator, shows cross-bar 61, extending between side bars 59, 60 on elongated arm 52, at their longitudinally-recessed location internally of the fracturing structure. At that longitudinal location, cross bar 61 is aligned longitudinally for fracturing compound-curvature distal-end 27 of ampoule 20. Cross bar 62 extends between the side bars 59 and 60 of elongated arm 52 at the entrance-opening into the elongated opening. Cross bar 62 can be seen in FIGS. 5A' and 5A"; and, is located for establishing an orientation for the elongated unitary container 18 near the entrance opening of hand-operable structure 50, so as to facilitate the described cross-bar 62 function at its recessed location; that is: to facilitate fracture of the distal-compound-curvature end 27 of ampoule 20 where located within the unitary container 18 of the inserted dual-test sterility indicator 19.

As shown in FIG. 5C, the longitudinally recessed location of fracturing cross-bar 61 contacts the outer generally-tubular portion of unitary container 18 of sterility test indicator 19, as located by support-platform 56; so as to transverse to the compound-curvature end of ampoule 20 as seen in FIG. 5C. The transversely-oriented force executed by cross-bar 61, as a result of urging closure at the entrance-opening of arms 51 and 52, is exerted against the exterior generally-tubular portion of container 18. That force distorts that tubular portion of container 18 inwardly; causing fracture of compound-curvature-end 27 (FIG. 1) of glass ampoule 20; releasing the liquid-contents of ampoule 20.

Before said fracturing operations, test sterility indicator 19, after sterilizer-chamber exposure, is first delivered for a "reference-reading" of cubic sidewalls 31, 32 of test chamber 30 as described in relation to FIG. 4; then, after release of liquid-contents of ampoule 20, as shown in FIG. 5C; the indicator is again inserted in chamber 33 of FIG. 4, with the same orientation of side walls 31, 32 as used for determined reference-reading, being used for spectroscopic quantitative chemometric measurements of the liquid-contents; carried out at approximately the prescribed temperature thirty-seven degrees Centigrade, plus or minus one degree Centigrade, established by block 34 at FIG. 4.

A touch-style keypad, as described in relation to later external views of spectroscopic analyzing equipment is used to enter test set-up information and operating parameters into microprocessor 40, as shown in FIG. 4. An external printer port provides for connecting a printer, as described later herein, to provide for recording test results. Block 34 of FIG. 4 is maintained at the prescribed temperature for spectroscopic measurements of test-indicators. After the reference reading and fracturing of the compound-curvature end 27 of ampoule 20 for release of its liquid contents, the test indicator will then be reinserted, with the same orientation into opening 33 of block 34; for establishing the prescribed temperature before proceeding with spectroscopic quantitative analysis.

Figure 6:
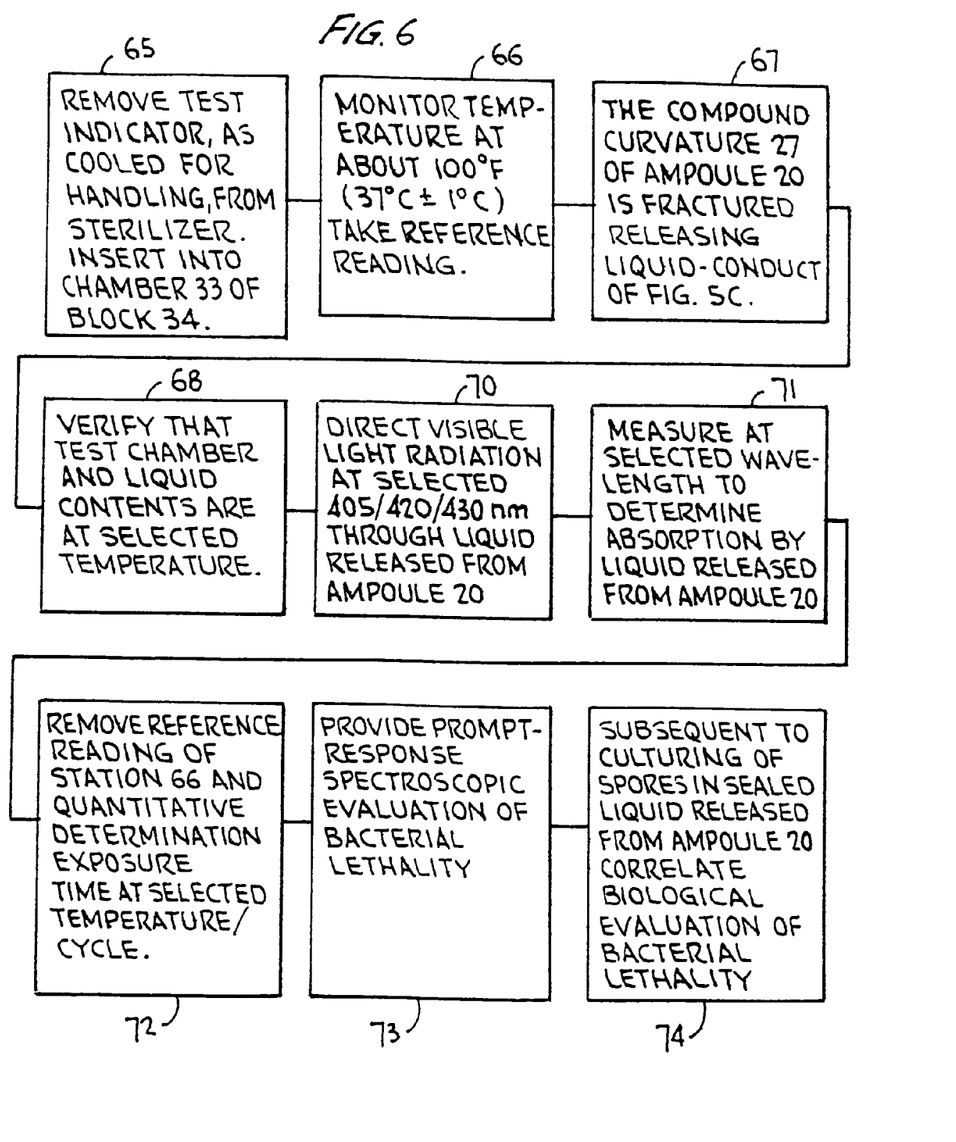
FIG. 6 is a box-diagram flow-chart for providing an overall description of steps of the invention for prompt-response spectroscopic evaluation of bacterial-lethality and for correlating biological evaluation of bacterial-lethality, in which both evaluations utilize contents of a single multiple-component integral-structure test-indicator of the invention.

Steps in carrying out the measurements of the invention are described in relation to the box-diagram flow-chart of FIG. 6. At Station 65, after cool-down of an exposed test-indicator, 19 of FIG. 3 to approximately one hundred degrees Fahrenheit, is inserted into temperature-controlled block 34 of FIG. 4. At Station 66, the temperature of the test indicator is established to the range of thirty-seven degrees Centigrade, plus or minus one degree Centigrade; verified by thermopile 41, as described in relation to FIG. 4 for directing to microprocessor controller 40. A "reference-reading" determination is made, based on the absorption of the selected visible-light wavelength during passage through the two parallel side walls 31, 32 of empty test chamber 30. After that reference-reading determination, the test indicator is withdrawn and inserted into fracturing-structure 50, as previously described in relation to FIGS. 5A, 5A', 5A", and FIG. 5B and 5C.

At Station 67 of FIG. 6, the compound-curvature end 27 of ampoule 20 is fractured as described above in relation to FIG. 5C. Polymeric-mesh sieve 26 screens the liquid-contents, as released from ampoule 20, preventing any large pieces of glass, as fractured from the compound curvature end 27 of ampoule 20, from entering test-chamber 30; which prevents possible distortion of the spectroscopic measurements of visible light absorption, as above-described, leading to a prompt-response spectroscopic evaluation of bacterial-lethality. The liquid-contents released from ampoule 20 move through the configuration 29 (FIG. 2) of spore-ladened substrate 28 to occupy test chamber 30; while, also, remaining in contact with substrate 28.

At Station 68 of FIG. 6, the temperature of the liquid-contents in test chamber 30 is coordinated with the temperature of block 35 by thermopile 43 of FIG. 4, in order to determine if any change in temperature occurred as a result of release of the liquid-contents of ampoule 20. When the prescribed temperature of thirty-seven degrees C, plus or minus one degree C, is verified, spectroscopic quantitative chemometric measurements of reaction product, if any, for bacterial-lethality can commence. At Station 70, narrow band visible-light, of a selected narrow-band dominant wavelength selected from the group consisting of 405 nm, 420 nm, and 430 nm, from light-source 35 (FIG. 4) is directed, through the liquid-contents, as released from ampoule 20, which occupy test chamber 30.

Test-chamber 30 presents a rectilinear cubic-shape, presenting two pairs of confronting parallel rectilinear side walls, interconnected by a distal end wall of the same configuration; as earlier described. At Station 71, absorption of the selected wavelength visible-light during passage through the liquid held in test-chamber 30, is measured by photoelectric-diode sensor 36 (FIG. 4). That is an absorption of the selected wavelength by the formulated organic-chemical solution, or by the reaction-product thereof, if any, will provide a responsive determination of time at the selected cycle temperature, as exposed during the sterilizing cycle where said indicator was located in the sterilizer chamber.

At Station 72, the spectroscopically measured total absorption of the selected visible-light wavelength is adjusted, by taking into account the earlier reference-reading absorption by the same opposed-parallel side walls of empty chamber 30, as determined at Station 66; that reference-reading is carried-out separately for each test-chamber of a unitary container 18 of an individual dual-test indicator 19, as used in a sterilizer load. A "prompt-response" spectroscopic evaluation of the bacterial-lethality, is then available at Station 73 of FIG. 6; which is carried out prior to establishing and maintaining culturing conditions of the sealed spores in the exposed liquid-contents, for a biological-evaluation of bacterial-lethality. A pH indicator is included in the liquid-contents as sealed in ampoule 20 in order to facilitate correlating those two evaluations of bacterial-lethality.

Bromcresol Purple is the preferred pH indicator for use in formulating the liquid-media 21 of the invention for ampoule 20. Bromcresol Purple does not effect the spectroscopic, nor the biological, evaluations of bacterial-lethality; and, Bromcresol Purple specifically enables, and provides for, biological verification of an earlier spectroscopically-measured evaluation, which is carried out at Station 74 of FIG. 6. That biological-evaluation provides a clearly visible change-in-color, if live spores exist during culturing the released liquid-contents of ampoule 20; if live spores do not survive the exposure to the selected cycle, there is no change in color.

Such biological-evaluation using the Bromcresol Purple pH indicator correlates directly with the prompt-response spectroscopic-evaluation of bacterial-lethality. That direct correlation is available because each testing is carried-out, in the same manner, utilizing contents within the same test-indicator, free of opportunity for ambient contamination. Combining a prompt-response evaluation of bacterial lethality and a biological-correlation of sterilizing effectiveness, using contents of a single multiple-component test-indicator 19, enables classification of that dual-test sterility indicator as a "biological-test-indicator" for saturated-steam sterilizing cycle effectiveness.

Figure 7A:
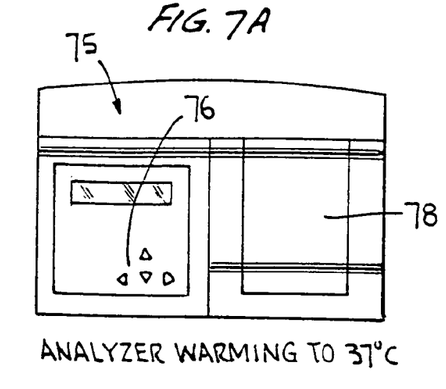
FIGS. 7A through 7F are perspective schematic views of equipment for describing sequential steps utilizing operational and control equipment of the invention as referred to in relation to FIG. 4, for prompt-response spectroscopic-chemometric evaluations of bacterial-lethality and recording related data in accordance with the invention.

FIGS. 7A, 7B, 7C, 7D, 7E and 7F are perspective exterior views spectroscopic analyzer equipment of the invention using the micro-processing controller 40 of FIG. 4, for user interface display entries and for data output for printing. FIG. 7A presents analyzer 75, with keypad 76 for digital entry of pertinent data; and, also, a closure door 78; used for shielding ambient electromagnetic radiation from entering into the measurements for a prompt-response spectroscopic-quantitative chemometric determination of sterilizing efficiency. With door 78 closed, the temperature selected for spectroscopic measurements, such as thirty-seven degrees Centigrade, plus or minus one degree Centigrade is established for reference-reading of a pair of opposed parallel walls of for test chamber 30; and also, for spectroscopic absorption evaluation of released liquid contents of ampoule 20; the latter being measured with the test-chamber walls being oriented identically as for the response-reading.

Figure 7B:
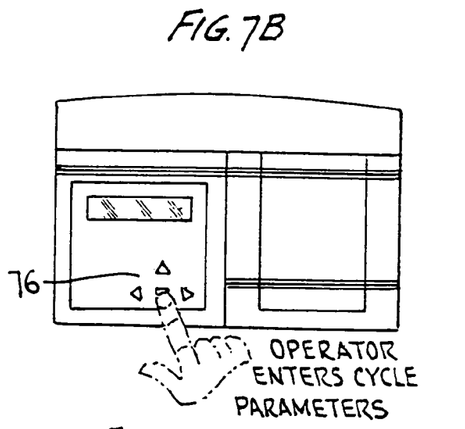

At display 76, of FIG. 7B, the operator digitally enters data covering the temperature and time at that temperature prescribed for the recently-completed saturated-steam sterilizing cycle; which data are to be associated with the record of the prompt-response spectroscopic-evaluation of bacterial-lethality. That is, hospitals and other health institutions, generally require, for record purposes, certain data to be set forth, such as: the date of the cycle operation, the saturated-steam cycle time (including air evacuation time), and the selected temperature for the saturated-steam sterilizer cycle; coded identification of the sterilizer itself is preferably set forth; and, information as to years of service, and dates of maintenance of the sterilizer can also be provided.

Figure 7C:
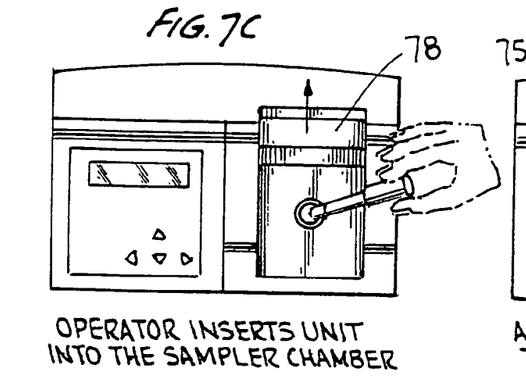
Figure 7D:
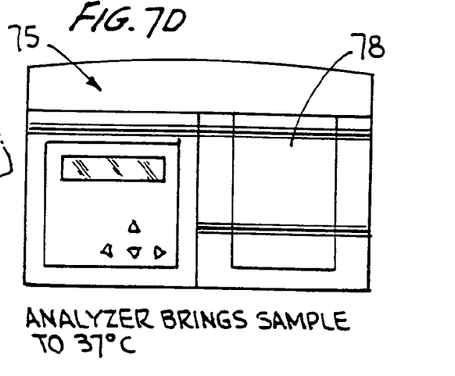
Figure 7E:
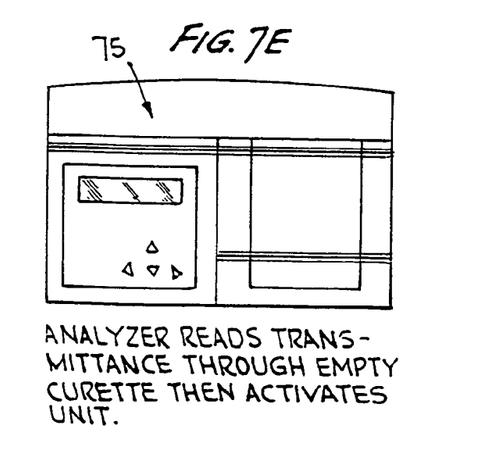

In FIG. 7C, door 78 is lifted by the operator, for inserting an exposed test-indicator. In FIG. 7D, door 78 is closed to prevent any interference, by ambient radiation, with spectroscopic measurements. The temperature of test chamber 30 is measured and brought, as described earlier in relation to FIGS. 4 and 6, to the selected temperature, before proceeding. The reference-reading measuring procedure is carried out at FIG. 6E; before removal of the indicator for fracturing release of the liquid-contents from ampoule 20. The operator obtains a reference reading of absorption of the selected visible-light wavelength through a pair of opposed side walls (31, 32) of empty test-chamber 30; as the indicator is inserted in chamber 33 of FIG. 4.

That reference-reading is based solely on the specific opposed-pair of rectilinear walls of the specific test-indicator, as positioned while test-chamber 30 is free of any liquid-contents from ampoule 20. It should be noted that a reference-reading could vary slightly from test indicator to test indicator; or, could vary by positioning a single test-indicator differently for transmission through a differing pair of test-chamber walls for the reference-reading the one later spectroscopic evaluation. The reference-reading is therefore repeated for each test indicator 19 to be evaluated, first, as inserted; then, that same orientation, of the same pair of reference-reading side walls, is carried out for purposes of accuracy of the later spectroscopic quantitative measurement of total visible-light absorption by exposed liquid contents, as released from ampoule 20, into test-chamber 30.

Figure 7F:
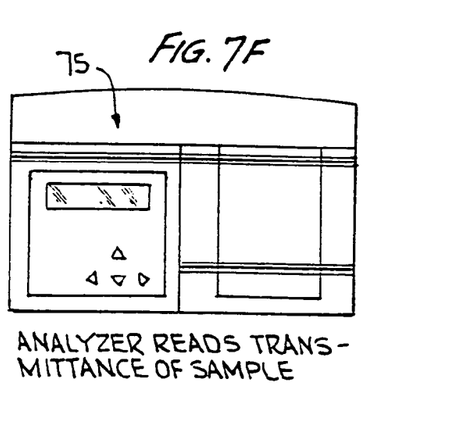

In FIG. 7F after temporary removal of the indicator for fracturing ampoule-end 27, as earlier described in relation to FIGS. 5A, 5A', 5A", 5B and 5C, for release of the exposed liquid-contents of ampoule 20; the test indicator is reinserted with the same orientation as previously used for the "reference" reading. The selected spectroscopic measurement temperature is again established which is verified by use of the thermopile, and other equipment, as described in relation to FIG. 4, before proceeding. The operator then measures total absorption of the selected wavelength visible-light by the exposed liquid-contents, as released from ampoule 20 into test-chamber 30. Analyzer 75, through microprocessor 40 (FIG. 4) compensates that measured absorption by the amount of the "reference-reading" as obtained earlier.

The resulting compensated spectroscopic absorption of the selected visible-light wavelength by liquid-contents, as exposed in sealed ampoule 20 during the sterilizing cycles; and, released, provides a prompt-response bacterial-lethality evaluation. The carbohydrates are formulated, in accordance with the invention, to be responsive to the selected cycle temperature and the time at that temperature, in accordance with presently accepted standards; and as experienced by contents of ampoule 20 as exposed, where located in the sterilizer chamber. That responsive temperature and time at that temperature measurement is based on the exposure of the liquid-contents before release from ampoule 20;. That prompt-response independent of any brief contact with substrate 28 before such qualitative chemometric measurement of glucosamine reaction-product, if any; and, is independent of use of the earlier described pH indicator Bromcresol Purple which is present for later culturing and biological evaluation of bacterial-lethality.

Figure 8A:
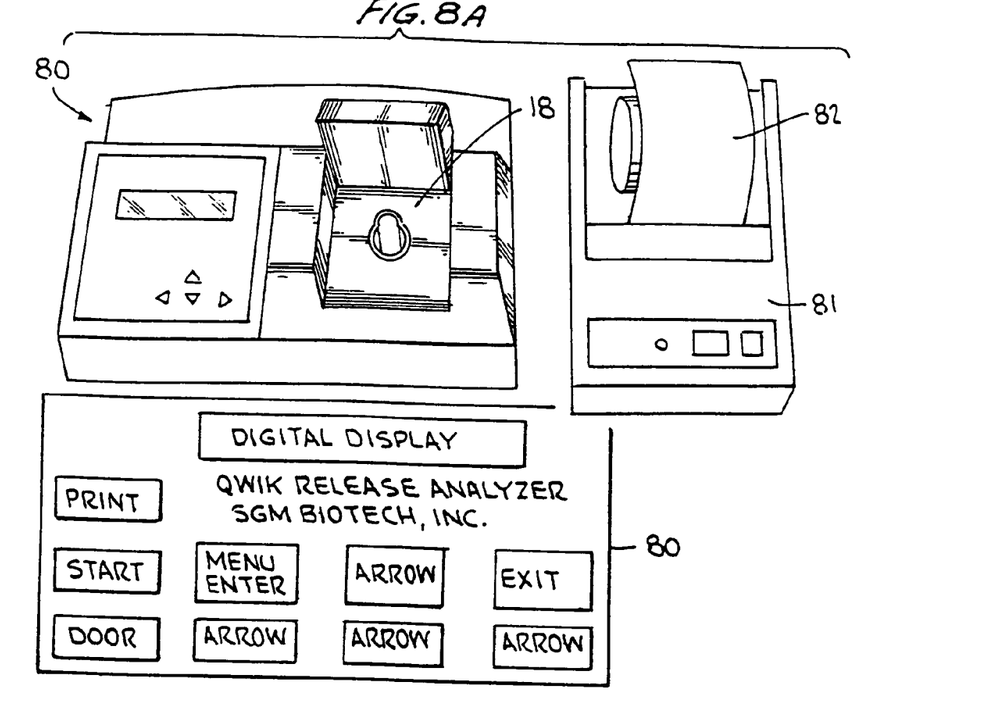
FIG. 8A is a perspective view for a describing printout of a spectroscopic-chemometric quantitative analysis of the invention utilizing microprocessor control as shown schematically in FIG. 4 for coordinating spectroscopic measurements.
Figure 8B:
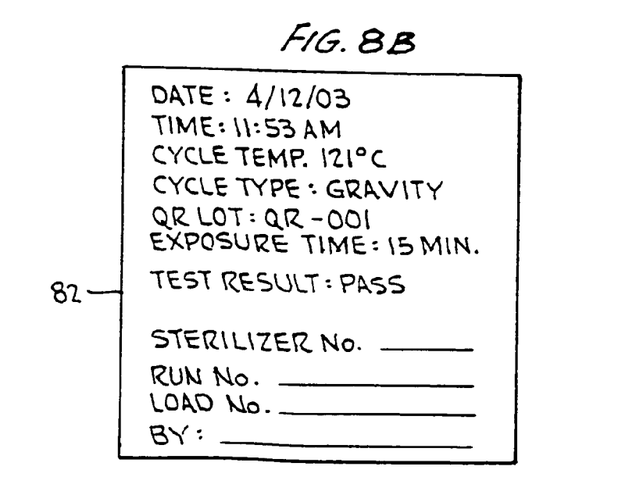
FIG. 8B is a controlled print-out record sheet presenting operational data covering spectroscopic-evaluation of bacterial-lethality, in accordance with the invention, along with identification of the saturated-steam sterilizing cycle.

FIG. 8A and FIG. 8B are concerned with operational control of an analyzer, as shown in FIG. 7, upon completing spectroscopic chemometric quantitative-analyses of the exposed organic-chemical-constituents of liquid-contents of ampoule 20, as released; and, with providing for microprocessor control of tabulated recording of entry data and measurement results. Chemical reaction product, if any, due to exposure of organic constituents of liquid-contents, involves a combination of the glucose and amino acid at the soytone to form glucosamine. The constituents are selected and formulated, in accordance with the invention, such that formation of that reaction-product is quantitatively responsive to temperature and time-at-that-temperature in accordance with present standards for the selected cycle; and, as experienced by the exposure of the test-indicator, where located in the sterilizer chamber during that selected saturated-steam cycle.

Spectroscopic chemometric quantitative-analysis of that exposure; and, therefore of bacterial-lethality, is available promptly upon completion of the above enumerated steps, after carrying-out the selective cycling; and, that spectroscopic evaluation, does not disturb later spore-culturing and biological-evaluation. It is significant that the organic constituents as formulated for ampoule 20, and the spores on substrate 28 are both exposed separately during the cycle; and, that bacteria of the load are exposed in the same manner; that is, free of any contact with a culturing material. Whether or not exposed, or only partially exposed, where located in the sterilizer chamber, the liquid-contents of ampoule 20, as released, are capable of culturing live spore growth, if any, and providing a subsequent biological evaluation of bacterial-lethality, or degree of absence thereof. And, both evaluations utilize the same contents, free of possible ambient contamination; that is, the biological evaluation of those contents will also indicate if full-intended exposure was experienced; and, whether partial or no exposure was experienced; if either of the latter occur, that will require recycling with a suitably-selected saturated-steam sterilizing cycle.

FIG. 8A shows analyzer 80 with door 78 open, a detailed digital display 80, for computer printout 81 for print-out of spectroscopic analyzing results. FIG. 8B presents details of record sheet 82, as printed by microprocessor 40 control of the printer; and, includes results of the spectroscopic quantitative chemometric evaluation based on level of absorbed visible-light. The date and time data of print-out record sheet 82 are controlled by the analyzer. The cycle temperature, for example: 121° C. (250° F.) refers to the temperature, as measured in the discharge line from a thermostatic valve for a saturated-steam sterilizer, after air evacuation. The desired temperature for bacterial-lethality is established by incoming pressurized saturated-steam, as air is driven from the chamber, from the goods to be sterilized, and from dual-test sterility indicator(s) 19, where located in the sterilizer chamber.

"CYCLE TYPE: GRAVITY" refers to the saturated-steam flow which is introduced at an upper level into the sterilizer chamber, with lower removal of air and condensate from the chamber relying, at least in-part, on the force of gravity. The "Lot" number and Exposure time are provided in response to information supplied the analyzer before start of spectroscopic analyzing operations. The total time of a cycle starts with closure of the sterilizer door, such that that "timing" includes air evacuation time; however, the time at temperature, for a selected cycle, commences only when such air evacuation has been completed, as discussed in further detail earlier; and, later herein.

Print record 82 of FIG. 8B indicates the spectroscopically measured TEST RESULT "Pass" or "Fail"; a result achieved independently by microprocess control of analyzer 75; is that independent determination adequately provided for proper record keeping purposes; along with the other recorded data. Remaining open-space below the "Test Result" on print record 82 can be used for further identification, such as the identification number and/or chamber location of the "Prompt-Response" dual-test-indicator(s); and should, include language identifying the health institute or other facility, and the name of the analyzer operator.

Certain of the additional information for the open space below the "Test-Result" of record 82, can be supplied by microprocessor control or by digital entry at the digital-display panel; and should be entered before starting analyzer operations. Specifically, that additional information identifies: the Sterilizer identification number; the number of the "Run" on that Sterilizer; the "LOAD" identification number or other designation; and, the name of the operator carrying out the sterilizing cycle.

Figure 9:
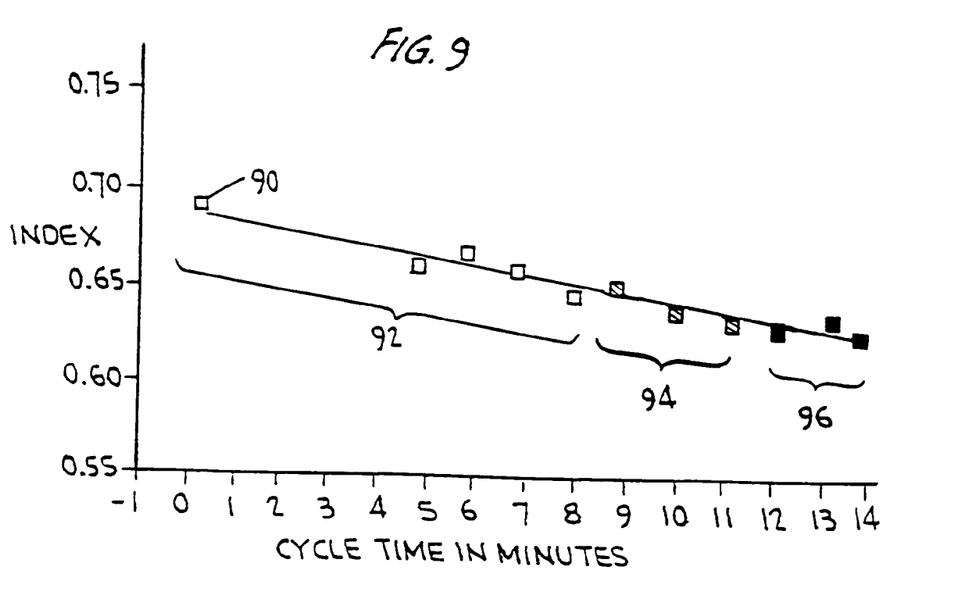
FIG. 9 is a graphical presentation for describing test results validating the correlation between prompt-response spectroscopic-evaluations of bacterial-lethality and cultured biological-evaluations, in accordance with the invention, by timed-interval interruptions of multiple saturated-steam cycles, with each cycle utilizing an individual sealed test-indicator of the invention, at each such interval, for obtaining graphically presented data.

The graphical data gathered for FIG. 9 substantiates that the procedures for verifying the direct correlation between spectroscopic quantitative chemometric evaluation of bacterial-lethality, and the subsequent cultured biological-evaluation of bacterial-lethality are correct; and, can be carried out periodically for a given installation. Those procedures involved multiple separate tests, each with separate dual-test indicators as above described; each such test being carried out with components and contents confined to avoid contamination, in each dual-test indicator, as described above. The data for FIG. 9 were gathered by timed interruptions of multiple individual saturated-steam cycles; each of which was separately, and properly, operated at a temperature preferably selected from the group of 205° F. and 270° F.; until a selectively timed interruption of each individual cycle.

Referring to FIG. 9, the first square 90, and the following four squares, at differing cycle times which cycles are designated as a group, as 92. Each of those squares is blank; interruption of each individual cycle for measurement at each of those times, indicated that air was continuing to be evacuated; such that the selected sterilization temperature had not yet been achieved. That is, evaluations, of those cycles at those times of interruption, designated as a group by 92, indicate that no significant time/temperature dependent bacterial-lethality had occurred; that indication resulted when measured by both spectroscopic and by biological-culturing evaluations.

The "shaded" squares, at three differing times, for each cycle forming another group designated by reference number 94, represent measurements made by interrupting each sterilizer cycle at each of three-designated cycle-time intervals. That is, an interrupted cycle reading was taken at slightly in excess of eight and a half minutes; a reading was taken of another interrupted cycle at a time of about ten minutes, and reading of another interrupted cycle was taken at eleven minutes. Each of these yielded an evaluation, by both spectroscopic evaluation and by biological culturing evaluations, that the same level of partial lethality of the spores has been accomplished, at each such measurement interval of the cycle.

The solidly-blackened group of squares of FIG. 9 designated 96, start with a cycle interrupted after passage of twelve minutes upon reaching the desired temperature (air evacuated); and, later with interrupting cycles at greater time intervals up to fifteen minutes; each time interval being at or after completion of air evacuation. Evacuation at times of those blackened squares, for a given saturated steam sterilizing system, indicate desired bacterial-lethality, by both spectroscopic evaluations and biological-cultured evaluations, at each of those times. That is, a cycle carried-out for at least twelve minutes, at 121° C. (250° F.), after completing air evacuation produces intended sterilizing effectiveness. Evaluations of cycles interrupted at greater time intervals after first establishing the selected temperature, upon completion of air evacuation, also verify the desired sterilizing effectiveness; and, some saturated-steam sterilizing systems may require a designated time up to about fifteen minutes. Saturated steam sterilizing system carried out at 220° F., can require times of about three to about five minutes. An indication of total time for sterilizer-door closure would require adding the air evacuation time.

Spectroscopic and biological evaluations, indicated by the graph of FIG. 9, are directly correlated by using a dual-test-sterility-indicator, free of contamination in accordance with earlier-described concepts. For example, bacterial-cultured biological-evaluation after twelve minutes of the 250° F. cycle verifies the spectroscopic evaluation of bacterial-lethality. Also, that including a pH indicator, such as Bromcresol Purple, in the sealed indicator does not change results of the evaluations of bacterial-lethality; or, of any of the interrupted cycle evaluations.

TABLE I

Test Indicator Data

Cap 14

Polymer: Polypropylene
Supplier: Union Carbide
Diameter: 0.496"
Height: 0.530"

Filter 17

Surgical Kraft Paper
Ethypel MD 3
Wet Brush Strength: 80 kPa minimum
Supplier: Arjo Wiggins
        Charleston, SC 29492

Ampoule 20

Borosilicate Glass: Type I
Thickness: 0.27 mm
Exterior Diameter: 6.75 mm
Overall Length: 42 mm
Supplier: Kimble Glass
        Fullerton, CA 92635

Sieve 26

Monofilament Mesh
Polymer: Polypropylene
Supplier: Franklin Products
        Rockaway, NJ 07866

Substrate 28

Special Purpose Cellulose Filter Paper
Caliper: 0.19 mm
Supplier: Schleicher and Schuell
        Keene, NH 03431
Spores: *Geo Bacillus stearothermophilus*
Supplier: SGM Inc.
        Bozeman, MT 59715

Container 18

TPX ® Polymethylpentane Polymer
Supplier: Mitsui Chemical, USA
Polybutylene Terephthalate (PBT)
Supplier: Eastman Chemical Inc.
Polypropylene/H.D. Polyethylene
Supplier: Union Carbide Corp.
Tubular Outer Diameter ⅝"
Overall Container Length (including Test Chamber 32): 2¼"

Test Chamber 30

Diagonal Diameter: about ⅝"
Square-Rectilinear Side Walls: ¼" by ¼"

Block 35

2" cubic configuration;
Conductive Metal

Hand-Operable Fracturing Structure 50

Elongation arms:
Length: 2½"
Width: ¾"
Polymer
Polypropylene
Polypropylene/Polybutylene
Supplier: SGM Biotech, Inc.
        10 Evergreen Drive, Suite #E
        Bozeman, MT 59715

TABLE II

Liquid-Media 21

Aqueous Solution:

Volume 0.82 ml
Supplier: SGM Inc.
        Bozeman, MT 59715

Chemical-Reaction Temperature/Time Dependency Constituents

| Constituent | Grams/liter |
| --- | --- |
| Glucose | 5.0 |
| Tryptone | 8.5 |
| Soytone | 10.0 |
| Soluble Starch | 1.0 |
| Yeast Extract | 0.5 |

Selected pH indicator Bromcresol Purple 0.0024 G/R

TABLE III

SPECTROSCOPIC ANALYZER

Supplier: SGM Biotech, Inc.
        10 Evergreen Drive, Suite E
        Bozeman, MT 59715

COMMERCIALLY-AVAILABLE ANALYZER COMPONENTS

LED #43    Preferred Narrow-Band Dominant Wavelengths 405 nm
420 nm
430 nm Photo Electric Diode #41 - Preferred Wavelengths 405 nm
420 nm
430 nm Specific materials and dimensions for apparatus, indicator structure, method of assembly steps, and sequence of use and analyzing operational steps have been set forth in detail so as to enable a person skilled in the art, to which the disclosure pertains, to make and use invention. However, it should be recognized that, in the light of above written description, a person skilled in that art, could minimally and selectively modify certain disclosed specifics of the above disclosure, in attempting to avoid patent infringement, while continuing to rely on, and continuing to the above-disclosed principles of the invention. Therefore, for purposes of determining the extent of valid patent coverage for the disclosed subject matter, reference should be made to the appended claims, which should be construed by taking into consideration the above-detailed disclosure methods, apparatus, products, and principles of operation of the invention.

The invention claimed is:

1. A manually-operable apparatus, for
   i. fracturing a compound-curvature end of an elongated unitary sealed glass ampoule located within an elongated-unitary polymeric container part of the multiple-component integral-structure dual-test sterility-indicator, wherein said elongated unitary sealed glass ampoule extends longitudinally internally of said elongated-unitary polymeric container and is fabricated from transparent glass material capable of being fractured by mechanical force being applied through a generally-tubular polymeric wall portion, from externally of said elongated-unitary polymeric container, for release of sealed liquid-contents thereof, which as formulated include (a) an aqueous solution of organic materials, including (i) glucose, (ii) tryptone, (iii) soytone, (iv) soluble starch, and (v) yeast extract, formulated to
(b) react responsively to both temperature and time-at-that-temperature, as experienced where said elongated-unitary polymeric container is located within a sterilizer chamber during carrying-out of a selected saturated-steam cycle,
(c) culture growth of live-spores, as formulated, and, also
(d) culture growth of live-spores, if any, as responsively-reacted by exposure to said selected cycle, while further including
(e) an organic pH indicator Bromcresol. Purple which is non-responsive to exposure to said cycle and capable of indicating live spore growth, if any, after such exposure by
(f) responding to change in pH of such aqueous solution due to growth of live bacterial spores if any remain after such exposure, for
ii. releasing liquid-contents from said sealed-glass ampoule, into said elongated-unitary-container of said indicator, subsequent to
iii. exposure experienced as located within a sterilizing chamber, during a selected saturated-steam sterilizing cycle; with
iv. said fracturing apparatus being fabricated from high-strength polymer, and comprising
A. an elongated pair of substantially-rigid polymeric arms, extending the longitudinal length of said hand-operable apparatus, presenting
i. a unitary closed-end, and defining
ii. a longitudinally-opposite entrance-opening into an elongated substantially-centrally-located opening, extending longitudinally-internally between said elongated arms;
B. a polymeric-joinder located longitudinally of, and unitary with said pair of elongated arms, at said closed-end, providing for
i. hinge-action at said unitary closed end, enabling opening and closing movement of entrance-opening ends of said elongated arms, so as to dimensionally define said entrance-opening into said longitudinal-extending opening between said arms;
C. means dimensionally constraining opening-movement between said elongated-arms for defining said entrance-opening, including
i. a transversely-oriented constraining-arm, extending transversely from each said elongated arm, toward the respective remaining elongated arm, at a recessed location within said elongated internal-opening, between said pair of elongated arms, with
ii. interlocking means on each said transversely-oriented constraining-arm, within said opening, for
iii. interlocking with the respective remaining constraining-arms, for
iv. limiting maximum entrance-opening defined by distal entrance-opening ends of such arms, and enabling
v. selectively increasing and diminishing of said entrance-opening for receiving a dual-test indicator within said elongated arms for defining said elongated opening extending longitudinally between said elongated arms;
D. a pair of width-wise spaced longitudinally-extending side bars, extending on each said elongated arm from said entrance-opening into said longitudinal-interior substantially-centrally located opening between said arms, with
i. each said pair of side bars extending from contiguous to said entrance-opening of each pair of arms in the direction of said joinder closed-end thereof,
ii. said pair of side bars on one of said elongated arms inter-fitting longitudinally, within
iii. said pair of side bars on the respective remaining elongated arm, so as to provide for
iv. longitudinally-orienting, and substantially-rigidly positioning, an elongated unitary container, of said test-indicator, as inserted from said entrance-opening into an elongated-opening defined between said pairs of sidebars;
E. a pair of transversely-oriented cross-bar means
i. extending inwardly, toward a centrally-located axis, for said elongated internal opening, with
ii. a single cross-bar means being located at a location contiguous to an inwardly-located distal-end of said side bars, such location being selected to
iii. position said single cross-bar means at said location for said compound-curvature end of the sealed-glass ampoule which is to be fractured for releasing liquid-contents into said elongated-unitary-container, with
iv. the remaining respective cross-bar means of said pair, being located near the entrance to said-elongated opening defined between side bars, with
(a) each of said pair of cross-bars extending transversely inwardly toward said central axis, for longitudinally-stabilizing an elongated-unitary-container, as positioned by said pair of side bars, for carrying-out said fracturing of said sealed-glass ampoule; and
F. platform means,
i. located in transverse relationship to said central-axis for said longitudinally-extended interior opening between said elongated arms, for
ii. contacting a cubic-shaped test-chamber, defining said distal-end of said unitary-container, as inserted into said entrance-opening end of said elongated pair of arms, as positioned by said side bars, for
iii. locating said single inner-located cross-bar means aligned with said selected compound-curvature end for fracturing said compound-curvature end of said sealed-glass ampoule, by applying force,
(a) acting through said polymeric generally-tubular portion of said container, and
(b) exerted against said selected compound-curvature end of said sealed-glass ampoule, for
(c) fracturing said compound-curvature end, of said sealed-glass ampoule, as said end is located within
(d) said elongated polymeric generally-tubular unitary-container, disposed toward said unitary cubic-shaped test-chamber, for
(e) releasing liquid-contents of said ampoule, for
(f) occupying said test chamber, and for
(g) initiating spectroscopic quantitative chemometric measurements, for
(h) providing a prompt-response analysis of bacterial-lethality.
2. Manually-operable apparatus for
i. releasing liquid-contents of a unitary sealed glass ampoule into a unitary closed-end of an elongated unitary polymeric container of a multiple-component integral-structure, which includes selected bacterial-spores contiguous to sealed-glass ampoule for providing dual-test evaluations of bacterial-lethality, with ii. ampoule contents, as released by said manually-operable apparatus into said elongated-unitary-container, being (a) responsive to temperature and time at that temperature, as experienced by selectively-formulated media of said ampoule, as held within said unitary container during a selected saturated-steam sterilizing cycle, and, in addition being
(b) capable of nurturing growth of remaining live bacterial-spores, if any, both before and after experiencing said saturated-steam cycle, with iii. said elongated unitary polymeric container, comprising
(a) a unitary cubic-shaped test-chamber defining its closed longitudinal end, and
(b) a cup-shaped polymeric closure-cap at its remaining longitudinal end, iv. said bacterial-spores, ampoule, and formulated liquid-media being assembled within said elongated unitary container, for enabling v. dual-test evaluations of bacterial-lethality of a selected saturated-steam sterilizing cycle, as experienced where said dual-test indicator is located within a sterilizing chamber during carrying-out of said selected cycle; in which said manually-operable apparatus for releasing said sealed glass ampoule contents, comprise:

A. a pair of elongated arms longitudinally-oriented between a closed end and an entrance-opening end for said apparatus, presenting
i. hinge-action joinder means,
  (a) located at said closed end of said pair of arms, and
  (b) joining each longitudinal end of said pair of elongated arms of said manually-operated apparatus,
ii. said opposite longitudinal end of each of said pair of arms defining an entrance-opening providing access into an elongated interior between said arms with said elongated-interior, being
  (a) longitudinally-directed, including
  (b) a substantially-centrally-located axis extending between ends of such elongated-interior; with
B. said entrance opening for said arms being operable for opening and closing movement, about said hinge-action joinder means at the remaining longitudinal end of said elongated arms; with
C. a pair of elongated side-bars
i. extending-longitudinally internally on each of said pair of arms, from contiguous to said entrance-opening
ii. located at a selected transverse-width dimension on each said arm, with
iii. each of said pair of side-bars extending from a location contiguous to said entrance-opening, and cooperatively defining
iv. an elongated channel-shaped means, extending longitudinally inwardly from contiguous to said entrance-opening internally of said elongated-arms, for
v. orienting and stabilizing said elongated polymeric unitary container, of said dual-test indicator-structure, longitudinally-internally of said pair of elongated arms;
D. a pair of protruding cross-bar means for orienting and stabilizing longitudinal orientation of said elongated container, with
i. said protruding cross-bar means extending width-wise between a single pair of said inwardly-directed side-bars on a single arm, with
  (a) a single protruding cross-bar means of said pair being located contiguous to said entrance-opening longitudinal end of said pair of elongated arms, and with
  (b) the remaining protruding cross-bar means of said pair being located contiguous to said internally-located longitudinally-end of said side-bars, at a longitudinal location
  (c) oriented toward said compound-curvature closed end of said sealed ampoule to be fractured, and with,
  (d) each said protruding cross-bar means having a rounded-outer-configuration, for
  (e) contacting said generally-tubular container, as
  (f) inserted into said elongated internal opening defined by said pair side-bar means;
E. platform means transversely-oriented internally within such elongated-interior defined by said elongated arms, at
i. a recessed location within said elongated interior, predeterminedly spaced longitudinally from said entrance opening for said elongated arms, for providing
ii. a transversely-oriented support for said cubic-shaped closed-end of said test-chamber of said elongated unitary container, for
iii. establishing a predetermined longitudinal location for enabling internally-located providing cross-bar means, to be
iv. directed toward said compound-curvature end of said ampoule within said generally-tubular portion of said container, such that
v. closure at said entrance-opening of said elongated arms, causes
  (a) fracturing of said compound-curvature-end of said sealed-glass ampoule,
  (b) releasing said ampoule contents into said elongated unitary-container, for
  (c) contact with said spores of said spore-ladened substrate within said container, while also
  (d) occupying said unitary cubic-shape test chamber at the closed-end of said container, so as to enable
F. a prompt-response spectroscopic quantitative chemometric measurement of reaction-product, if any, of said ampoule liquid-contents which is responsive to temperature and time at that temperature experienced during exposure to said selected cycle, with
i. said measurement being based on absorption of a selected dominant wavelength narrow-band visible-light having a frequency selection from the group consisting of 405 µm, 420 µm, and 430 µm, for promptly-indicating bacterial-lethality of said cycle, and while
ii. said spores and released ampoule-contents remain sealed within said unitary-container of said integral structure, providing
iii. a subsequent correlated biological-test of bacterial-lethality utilizing said spores and released ampoule-contents, as confined in said unitary container, for nurturing life-spores, if any.

* * * * *